United States Patent
Jackson

(10) Patent No.: US 12,338,434 B1
(45) Date of Patent: Jun. 24, 2025

(54) METHODS AND MATERIALS FOR DISCOVERY OF FUNCTIONAL LIGANDS TO MOLECULAR COMPLEXES

(71) Applicant: Base Pair Biotechnologies, Inc., Pearland, TX (US)

(72) Inventor: George W. Jackson, Pearland, TX (US)

(73) Assignee: BASE PAIR BIOTECHNOLOGIES, INC., Pearland, TX (US)

( * ) Notice: Subject to any disclaimer, the term of this patent is extended or adjusted under 35 U.S.C. 154(b) by 1210 days.

(21) Appl. No.: 16/927,346

(22) Filed: Jul. 13, 2020

Related U.S. Application Data

(63) Continuation of application No. 16/369,716, filed on Mar. 29, 2019, now abandoned, and a continuation-in-part of application No. 15/920,343, filed on Mar. 13, 2018, now abandoned.

(60) Provisional application No. 62/470,600, filed on Mar. 13, 2017.

(51) Int. Cl.
  *C12N 15/10* (2006.01)

(52) U.S. Cl.
  CPC ................ *C12N 15/1048* (2013.01)

(58) Field of Classification Search
  CPC .................................. C12N 15/1048
  USPC ..... 435/6.1, 91.1, 91.31, 7.1; 536/23.1, 24.5
  See application file for complete search history.

*Primary Examiner* — Jane J Zara

(74) *Attorney, Agent, or Firm* — Equip LG; Christopher Quan

(57) ABSTRACT

This invention relates to methods and materials for discovery of functional ligands, particularly to methods and materials for selecting for functional ligands to molecular complexes, and more particularly to methods and materials for selecting for functional ligands to molecular complexes with metal ions, such as coordination complexes with metal ions. For example, functional ligands, such as aptamers, may be selected for specific and high affinity binding to coordination complexes of metal ions of interest, such as particular arsenic ions.

10 Claims, 1 Drawing Sheet

METHODS AND MATERIALS FOR DISCOVERY OF FUNCTIONAL LIGANDS TO MOLECULAR COMPLEXES

CROSS-REFERENCE TO RELATED APPLICATIONS

This application is a continuation of U.S. patent application Ser. No. 16/369,716, filed Mar. 29, 2019, entitled, "METHODS AND MATERIALS FOR DISCOVERY OF FUNCTIONCAL LIGANDS TO MOLECULAR COMPLEXES", which is a continuation-in-part of U.S. patent application Ser. No. 15/920,343, filed Mar. 13, 2018, entitled, "METHODS AND MATERIALS FOR DISCOVERY OF FUNCTIONCAL LIGANDS TO MOLECULAR COMPLEXES", which claims the benefit and priority of U.S. provisional patent application Ser. No. 62/470,600, filed Mar. 13, 2017, entitled, "METHODS AND MATERIALS FOR DISCOVERY OF FUNCTIONCAL LIGANDS TO MOLECULAR COMPLEXES". The contents of the foregoing applications are hereby incorporated by reference in their entireties.

COPYRIGHT NOTICE

A portion of the disclosure of this patent document contains material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

FIELD OF THE INVENTION

This invention relates to methods and materials for discovery of functional ligands, particularly to methods and materials for selecting for functional ligands to molecular complexes, and more particularly to methods and materials for selecting for functional ligands to molecular complexes with metal ions, such as coordination complexes with metal ions.

BACKGROUND OF THE INVENTION

Aptamers, which are nucleic acid ligands capable of binding to molecular targets, have recently attracted increased attention for their potential application in many areas of biology and biotechnology. They may be used as sensors, therapeutic tools, to regulate cellular processes, as well as to guide drugs to their specific cellular target(s). Contrary to the actual genetic material, their specificity and characteristics are not directly determined by their primary sequence, but instead by their secondary and/or tertiary structure. Aptamers have been recently investigated as immobilized capture elements in a microarray format. Others have recently selected aptamers against whole cells and complex biological mixtures. Aptamers may also, for example, exhibit changes in their secondary and/or tertiary structure depending on whether it is complexed or uncomplexed with a target molecule.

Aptamers are commonly identified by an in vitro method of selection sometimes referred to as Systematic Evolution of Ligands by EXponential enrichment or "SELEX". SELEX typically begins with a very large pool of randomized polynucleotides which is generally narrowed to one aptamer ligand per molecular target. Once multiple rounds (typically 10-15) of SELEX are completed, the nucleic acid sequences are identified by conventional cloning and sequencing. Aptamers have most famously been developed as ligands to important proteins, rivaling antibodies in both affinity and specificity, and the first aptamer-based therapeutics are now emerging. More recently, however, aptamers have been also developed to bind small organic molecules and cellular toxins, viruses, and even targets as small as heavy metal ions.

Arsenic is an environmental toxin with severe consequences on human health. While the prevalence of arsenic in drinking water is more problematic in certain regions of the world than others, its toxicity is such that it is routinely monitored in water treatment facilities worldwide. Although arsenic exists in many different chemical forms in nature, it is found almost exclusively as arsenite (As(III) as $H_3AsO_3$) and arsenate (As(V) as $H_3AsO_4$) in water. As(III) was identified as one of the most harmful substances in water to human health, and is 60 times more toxic than As(V) or organic arsenic compounds. In 2001, the U.S. EPA and the World Health Organization lowered the maximum contaminant level (MCL) guideline for arsenic in drinking water from 50 to 10 ppb.

SUMMARY OF THE INVENTION

The present invention relates to methods and materials for discovery of functional ligands, particularly to methods and materials for selecting for functional ligands to molecular complexes, and more particularly to methods and materials for selecting for functional ligands to molecular complexes with metal ions, such as coordination complexes with metal ions. In general, functional ligands may be selected for and/or utilized for their ability to bind or complex to particular targets, and/or for the manner in which they bind or complex to particular targets, such as by binding to particular targets when in certain conformations or in a molecular complex, or vice versa. For example, numerous biomolecules, such as nucleic acids and peptides, take on varied secondary and tertiary structures in response to different environments or by associating with other molecules. Functional ligands may generally include biomolecules such as nucleic acids, such as single-stranded nucleic acids and double-stranded nucleic acids or combinations or regions of both, peptides, other biopolymers and/or combinations or modifications thereof, such as artificially modified nucleic acids, synthetic analogs and the like. The targets may be, for example and without limitation, small molecules, ions, molecular and/or coordination complexes, and/or combinations or portions thereof. In general, selection or discovery of functional ligands may be accomplished with SELEX methods or variations thereof.

In one aspect of the present invention, a method for selecting functional ligands may include providing a collection of functional ligands, introducing a target, where the target may be molecules which form coordination or molecular complexes with particular ions, such as metal ions. In general, small molecular or ionic targets, such as metal ions, may present difficulties for discovering functional ligands with sufficient specificity to discriminate between the target and other small molecular or ionic species. However, many chelating or other complexing agents exist which may display significant specificity to particular ions and may themselves present as targets for selecting functional ligands when in the context of binding particular ions or in the context of not binding the desired ions. This may be desirable to select functional ligands with specificity to the desired molecular complex which includes the desired ionic species that does not bind or binds with significantly less affinity to the molecular complex with an undesired ionic species bound or not bound to anything at all, since even highly specific chelating or other complexing agents may sometimes bind to other ionic species.

In some exemplary embodiments, functional ligands may be selected against targets that include a complexing agent specific and/or semi-specific to a desired ionic species bound and unbound to said ionic species, for example, simultaneously, sequentially or in parallel, such that functional ligands that bind to both the bound and unbound complexing agent may be eliminated and/or otherwise designated as non-specific to one or the other. The selection may also include the complexing agent bound to other ionic species rather than the desired ionic species to similarly eliminate and/or otherwise designate functional ligands that bind to the complex with the undesired species.

In some exemplary embodiments, functional ligands may be selected against complexing agents bound to specific valence states of a metal such that functional ligands may be selected that may discriminate between valence states of a metal. For example, it may be desirable to select for functional ligands to As(III) as opposed to other valence states, such as As(V), as As(III) is much more toxic to humans and both species may bind to arsenic-binding complexing agents.

In In general, variations to the binding conditions may also be employed, such as to detect variations in structural changes, binding affinity, cross-reactivity, detection limits, and/or any other appropriate variation. For example variations in binding conditions may include, but are not limited to, concentrations of the target molecules, inclusion of other target molecules, variation in pH, temperature, pressure, flow, electrical gradient, solvent, degree of complementarity between functional ligands and indicators, solute makeup/concentration, spacing of functional ligands, spacing between functional ligands and a substrate, and/or any other appropriate variation in binding conditions.

In some embodiments, the functional ligands included in a collection may be randomized or unknown. In other embodiments, at least one of the functional ligands may be selected previously for a known or suspected trait or characteristic, such as known binding to a particular target and/or any other known or suspected trait or characteristic. This may be desirable, for example, to efficiently utilize prior data or experimental results to speed up or narrow selection.

The present invention together with the above and other advantages may best be understood from the following detailed description of the embodiments of the invention and as illustrated in the drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

DETAILED DESCRIPTION OF THE INVENTION

Figure 1:
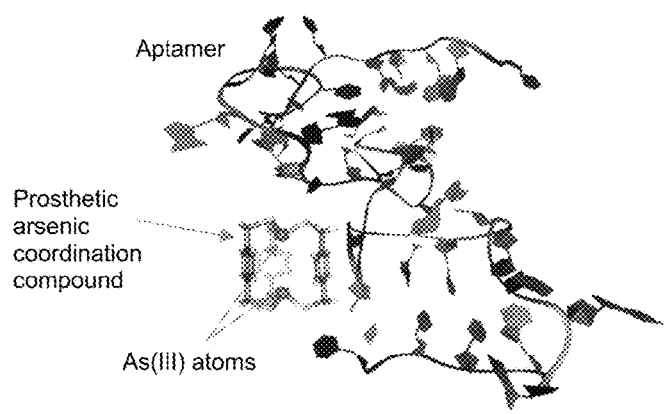
FIG. 1 illustrates an example of an aptamer binding to a coordination complex of a metal ion.

The detailed description set forth below is intended as a description of the presently exemplified methods, devices, and compositions provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

The present invention relates to methods and materials for discovery of functional ligands, particularly to methods and materials for selecting for functional ligands to molecular complexes, and more particularly to methods and materials for selecting for functional ligands to molecular complexes with metal ions, such as coordination complexes with metal ions. In general, functional ligands may be selected for and/or utilized for their ability to bind or complex to particular targets, and/or for the manner in which they bind or complex to particular targets, such as by binding to particular targets when in certain conformations or in a molecular complex, or vice versa. For example, numerous biomolecules, such as nucleic acids and peptides, take on varied secondary and tertiary structures in response to different environments or by associating with other molecules. Functional ligands may generally include biomolecules such as nucleic acids, such as single-stranded nucleic acids and double-stranded nucleic acids or combinations or regions of both, peptides, other biopolymers and/or combinations or modifications thereof, such as artificially modified nucleic acids, synthetic analogs and the like. The targets may be, for example and without limitation, small molecules, ions, molecular and/or coordination complexes, and/or combinations or portions thereof. Functional ligands may generally include biomolecules such as nucleic acids, such as single-stranded nucleic acids and double-stranded nucleic acids or combinations or regions of both, peptides, other biopolymers and/or combinations or modifications thereof, such as artificially modified nucleic acids, synthetic analogs and the like. Non-naturally occurring sequences of functional ligands, such as nucleic acids and nucleic acid analogs, such as aptamers, may also be useful by interacting with a target molecule in a manner not present in naturally occurring systems or situations, such as by, for example, not being already present or having a pre-existing function in a naturally occurring setting.

Other examples of functional ligands may include, but are not limited to, G-protein receptors, ion channels, promoter or enhancer elements of DNA, nucleic acid beacons/probes which exhibit conformational changes, and/or any other appropriate functional ligands with the desired structural/conformational changing properties.

In general, functional ligands may generally include nucleic acids, particularly single-stranded nucleic acids, peptides, other biopolymers and/or combinations or modifications thereof. Nucleic acid sequences may include naturally-occurring biomolecules such as ribonucleic acid (RNA), deoxyribonucleic acid (DNA), artificially modified nucleic acids, and/or combinations thereof. In general, modified nucleic acid bases may be utilized and may include, but are not limited to, 2'-Deoxy-P-nucleoside-5'-Triphosphate, 2'-Deoxyinosine-5'-Triphosphate, 2'-Deoxypseudouridine-5'-Triphosphate, 2'-Deoxyuridine-5'-Triphosphate, 2'-Deoxyzebularine-5'-Triphosphate, 2-Amino-2'-deoxyadenosine-5'-Triphosphate, 2-Amino-6-chloropurine-2'-deoxyriboside-5'-Triphosphate, 2-Aminopurine-2'-deoxyribose-5'-Triphosphate, 2-Thio-2'-deoxycytidine-5'-Triphosphate, 2-Thiothymidine-5'-Triphosphate, 2'-Deoxy-L-adenosine-5'-Triphosphate, 2'-Deoxy-L-cytidine-5'-Triphosphate, 2'-Deoxy-L-guanosine-5'-Triphosphate, 2'-Deoxy-L-thymidine-5'-Triphosphate, 4-Thiothymidine-5'-Triphosphate, 5-Aminoallyl-2'-deoxycytidine-5'-Triphosphate, 5-Aminoallyl-2'-deoxyuridine-5'-Triphosphate, 5-Bromo-2'-deoxycytidine-5'-Triphosphate, 5-Bromo-2'-deoxyuridine-5'-Triphosphate, 5-Fluoro-2'-deoxyuridine-5'-Triphosphate, 5-Trifluoromethyl-2-deoxyuridine-5'-Triphosphate, and/or any other appropriate modified nucleic acid base. It may generally be understood that the nucleoside triphosphates (NTPs) listed above may generally refer to any appropriate phosphate of the modified base, such as additionally, for example, monophosphates (NMPs) or diphosphates (NDPs) of the base. Embodiments of the SELEX method may generally be utilized to select or preselect for aptamers to be used in a collection. The basic SELEX protocol and aptamers are described in U.S. Pat. No. 5,270,163, entitled "Methods for identifying nucleic acid ligands," the entire contents of which are hereby incorporated by reference.

In one aspect of the present invention, a method for selecting functional ligands may include providing a collection of functional ligands, introducing a target, where the target may be molecules which form coordination or molecular complexes with particular ions, such as metal ions. In general, small molecular or ionic targets, such as metal ions, may present difficulties for discovering functional ligands with sufficient specificity to discriminate between the target and other small molecular or ionic species. Further difficulties may include generating directly binding functional ligands which may bind at an appropriate affinity. For example, arsenic may be dangerous in water sources at concentrations as low as 10 parts per billion (ppb) and thus a functional ligand may need an appropriately high relative affinity for a particular target, such as, for example, on the order of picomolar (pM) or nanomolar (nM) dissociation constants ($K_d$). However, many chelating or other complexing agents exist which may display significant specificity to particular ions and may themselves present as targets for selecting functional ligands when in the context of binding particular ions or in the context of not binding the desired ions. This may be desirable to select functional ligands with specificity to the desired molecular complex which includes the desired ionic species that does not bind or binds with significantly less affinity to the molecular complex with an undesired ionic species bound or not bound to anything at all, since even highly specific chelating or other complexing agents may sometimes bind to other ionic species.

Functional ligands selected or discovered by the methods of this invention may generally, for example, without limitation and without being bound to any particular theory, be utilized for detection, quantification, and/or other diagnostic applications, such as for detection of ionic species in fluids. For example, detection of ionic species, such as arsenic ions, may be utilized in detecting contamination in water sources, such as with lateral flow assays using the functional ligands as the detection agent (such as in the place of antibodies), fluorescence assays (such as with functional ligands which are formed as aptamer beacons which change conformation upon binding to their target), and/or any other appropriate detection technology.

In some exemplary embodiments, functional ligands may be selected against targets that include a complexing agent specific and/or semi-specific to a desired ionic species bound and unbound to said ionic species, for example, simultaneously, sequentially or in parallel, such that functional ligands that bind to both the bound and unbound complexing agent may be eliminated and/or otherwise designated as non-specific to one or the other. The selection may also include the complexing agent bound to other ionic species rather than the desired ionic species to similarly eliminate and/or otherwise designate functional ligands that bind to the complex with the undesired species.

In some exemplary embodiments, functional ligands may be selected against complexing agents bound to specific valence states of a metal such that functional ligands may be selected that may discriminate between valence states of a metal. For example, it may be desirable to select for functional ligands to As(III) as opposed to other valence states, such as As(V), as As(III) is much more toxic to humans and both species may bind to arsenic-binding complexing agents. FIG. 1 illustrates the possible interaction between an example functional ligand, shown as a nucleic acid aptamer, with a coordination compound bound to arsenic ions of a particular valence state and thus exhibiting a particular conformation recognized by the aptamer.

Figure 2:
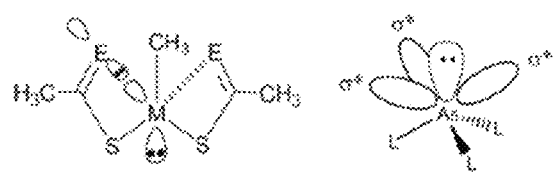
FIGS. 2, 2a and 2b illustrate examples of coordination compounds for metal ions.
Figure 2A:
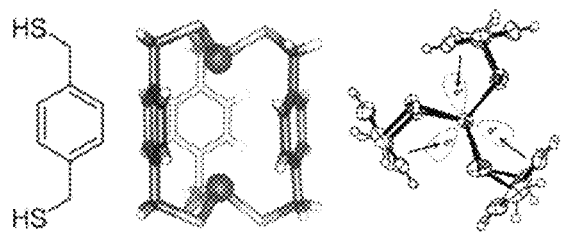
Figure 2B:
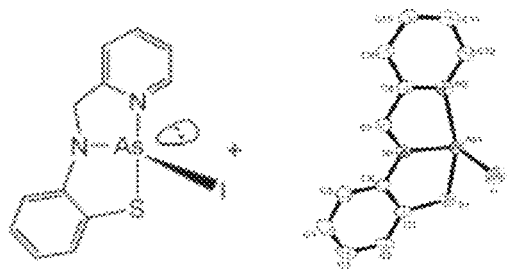

In some embodiments, chelating and/or other complexing agents may be utilized which exhibit specific conformations or other distinguishable structural features when bound to the desired ionic species as opposed to unbound states or states where bound to an undesired ionic species. In general and without being bound to any particular theory, chelating agents may be utilized that create trigonal-pyramidal coordination geometries with As(III) with a stereochemically active lone pair when coordinated by ligands with properly oriented lone pairs and/or stabilized by interactions with phenyl rings or similar molecular features. Examples and characteristics of such molecules and their interactions with As(III) are described by Vickaryous et al. (Vickaryous, W. J., Herges, R., Johnson, D. W.; "Arsenic-Interactions Stabilize a Self-Assembled As2L3 Supramolecular Complex"; Angew. Chem. Int. Ed. 2004, 43, 5831), which is hereby incorporated by reference in its entirety. Examples of chelating and/or complexing agents, such as for specifically or distinguishably binding As(III), may include, but are not limited to, thiol-containing molecules, such as organothiolate ligands as illustrated in FIG. 2, bis(mercaptomethyl) benzene (FIG. 2a), 2-(pyridin-2-yl)-2,3-dihydrobenzo[d]thiazole (FIG. 2b). Other examples include, but are not limited to, 4-(mercaptomethyl)benzoic acid, 1,4-benzenedimethanethiol, meso-2,3-dimercaptosuccinic acid, 2,3-dimercapto-1-propanesulfonic acid, 2,3-dimercapto-1-propanol, and/or any other appropriate chelating agent. It may further be desirable that the ionic state of the ionic species be maintained during selection and/or during a detection. In general and without being bound to any particular theory, antioxidants may be utilized to aid in maintaining the oxidation state of the ionic species (e.g. maintaining As(III) and preventing oxidation to As(V)), such as by using ascorbic acid and/or any other appropriate antioxidant.

In general and without being bound to any particular theory, a form of SELEX method may be utilized to select functional ligands, such as aptamers, against targets by providing a large pool or library of potential functional ligands, such as nucleic acids, which may be hybridized and/or otherwise reversibly immobilized to a substrate(s), such as by hybridizing nucleic acid members of the pool or library to docking oligonucleotides (docking oligos) on the substrate(s), such as through a constant hybridization region which may be included with all of the members of the pool or library. In general, the hybridization may be chosen or designed such that when a member of the pool or library binds to a target with sufficient affinity, it may dehybridize from the docking oligo, and thus become detached from the substrate(s). The detached members of the pool or library, bound to the target, may then be collected or otherwise sequestered from the non-binding members, such as by washing the substrate(s) and collecting the eluent. The binding members may then be analyzed for their composition and/or sequence, such as by sequencing (e.g. next generation sequencing) and/or any other appropriate method.

During the selection, targets may be exposed to the pool or library, such as in sequence. For example, when selecting for a molecular complex with a particular desired ionic species bound to a complexing agent, the unbound agent may be introduced first to elute members of the pool or library that may bind to the unbound agent, followed by introducing the bound (to the desired ionic species) agent to elute members which bind to the desired molecular complex but not to the unbound agent. Additional exposures may also be included, such as with the agent complexed with undesired ionic species, such that the eluted binders may be sequestered. In other embodiments, the pool or library may be exposed to the different targets separately, such as in parallel, and cross-binders may be identified after sequencing of binding members, such as to eliminate them as non-specific binders.

Multiple rounds of selection, such as with each previous rounds of binders, may be performed to concentrate the pool of binders with stronger binding members.

In general, when referring to attaching, immobilizing or otherwise associating functional ligands (including potential members from a pool or library) with a substrate(s), this may include use of docking oligos associated with the substrate(s) which then may hybridize to the functional ligands.

In some embodiments, the target(s) may be immobilized and/or tethered to a substrate and exposed to a pool or library. The members that bind to the target(s) may be retained through such binding on the substrate while the non-binders may be washed off or otherwise partitioned, such as by removing the substrate (e.g. magnetic beads removed from a fluid containing the pool or library). The binding members may then be collected and subjected to additional rounds of binding and/or sequenced/analyzed to determine their composition and/or sequence. In some embodiments, multiple different targets may be disposed on the substrate or, for example, multiple substrates may be utilized with a different target on each (e.g. multiple beads with each bead bearing a different target), such that a pool or library may be exposed to multiple targets simultaneously. This may, for example, be used to elucidate members of the pool or library which bind to multiple targets (e.g. copies of a member binding to more than one of the targets), or as an additional binding condition (e.g. presents competition between targets to the pool or library). Also, utilizing multiple targets simultaneously contacted with the same pool or library may be more efficient in time and/or cost savings. Additional details on performing a SELEX procedure on multiple targets simultaneously are described in U.S. Pat. No. 8,314,052, entitled "Methods for simultaneous generation of functional ligands," the contents of which is hereby incorporated by reference in its entirety.

In embodiments utilizing a solid substrate, the substrates used may be glass, ceramic or polymeric, and/or any other appropriate material. In general, it may be desirable to utilize a material that is convenient for attaching functional ligands, such as via docking oligos which may be, for example, formed on the substrate(s) with in situ synthesis, or targets. Polymers may include synthetic polymers as well as purified biological polymers. The substrate may also be any film, which may be non-porous or macroporous.

The substrate may be generally planar and may be of any appropriate geometry such as, for example, rectangular, square, circular, elliptical, triangular, other polygonal shape, irregular and/or any other appropriate geometry. The substrate may also be of other forms, such as cylindrical, spherical, irregular and/or any other appropriate form.

Appropriate ceramics may include, for example, hydroxyapatite, alumina, graphite and pyrolytic carbon.

Appropriate synthetic materials may include polymers such as polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. These synthetic polymers may be woven or knitted into a mesh to form a matrix or similar structure. Alternatively, the synthetic polymer materials can be molded or cast into appropriate forms.

Biological polymers may be naturally occurring or produced in vitro by fermentation and the like or by recombinant genetic engineering. Recombinant DNA technology can be used to engineer virtually any polypeptide sequence and then amplify and express the protein in either bacterial or mammalian cells. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

Any suitable substrate may be susceptible to adhesion, attachment or adsorption by functional ligands, such as by hybridizing to immobilized docking oligos. The susceptibility may be inherent or modified. In one example, the surfaces of substrates may be susceptible to adhesion, attachment or adsorption to nucleic acids or peptides/proteins. In another example, the surfaces of substrates may be susceptible to adhesion, attachment or adsorption to proteins or peptides and not to nucleic acids, or vice versa.

In one embodiment, a glass substrate may have a layer or coating of a material that promotes adhesion with targets, such as proteins, peptides or nucleic acids, materials that maybe charged, such as those that are positively charged, for binding target materials. Examples of charged materials include cellulosic materials, for example, nitrocellulose, methylcelluose, ethylcellulose, carboxymethyl cellulose, hydroxyethyl cellulose, methylhydroxypropyl cellulose; epoxies, PVDF (polyvinylidene fluoride); partially or fully hydrolyzed poly(vinyl alcohol); poly(vinylpyrrolidone); poly(ethyloxazoline); poly(ethylene oxide)-co-poly(propylene oxide) block copolymers; polyamines; polyacrylamide; hydroxypropylmethacrylate; polysucrose; hyaluronic acid; alginate; chitosan; dextran; gelatin and mixtures and copolymers thereof.

In other embodiments, if the substrate is not susceptible for attachment by charged materials, or may be susceptible only for attachment by wrongly charged materials, some areas of the substrate may have adhesives, binding agents, or similar attached, adsorbed or coated thereon. Examples of adhesives may include any suitable adhesives that bind the charged materials.

The functional ligands may be present on the substrate discretely or in clusters. The distance between the discrete functional ligands may be close or may be far apart and may usually be of different functional ligands. Clusters may be used for multiple spots of a single functional ligand. In general, the distance between placements may be chosen to aid in preventing direct interactions between adjacent functional ligands, to aid in preventing unwanted multiple binding events between a target and adjacent functional ligands, to aid in preventing interference of a binding event due to proximity to an adjacent functional ligand and/or in preventing any other applicable unwanted interactions.

In one embodiment, the substrate may be macroporous. Macroporous substrates may be desirable, for example, if the different functional ligands are very close together. Closely packed functional ligands may, for example, increase the efficiency of the utilization of a particular substrate. A macroporous substrate may be suited for balancing between efficiency and separation. For a macroporous substrate, the walls of the pores may be sufficient to separate even closely packed functional ligands if the pores are large enough to enable the binding process to occur within the pores.

Also, for macroporous substrates, the pores may have an average diameter greater than the average size of the target molecule(s) such that they may enter or partly enter the pores for binding events to occur. Hydrogels may also be useful for binding or anchoring functional ligands to the pores. Hydrogels may also fill the pores under fluid conditions and present a smooth surface for fluid flow while at the same time may keep the fluid from flowing through the pores.

The plurality of functional ligands may be arranged in any appropriate manner such as, for example, in circular or elliptical spots, square or rectangular spots, stripes, concentric rings and/or any other appropriate arrangement on the subject.

In some embodiments, the functional ligands may also be disposed, such as via docking oligos, on beads or other free-floating substrates. For example, glass beads, agarose beads (e.g. Sepharose), cellulose beads, and/or any other appropriate free floating substrate may be utilized. The beads or free-floating substrates may also generally be magnetic and/or otherwise adapted for separation from a fluid phase.

In general, variations to the binding conditions may also be employed, such as to detect variations in structural changes, binding affinity, cross-reactivity, detection limits, and/or any other appropriate variation. For example variations in binding conditions may include, but are not limited to, concentrations of the target molecules, inclusion of other target molecules, variation in pH, temperature, pressure, flow, electrical gradient, solvent, degree of complementarity between functional ligands and indicators, solute makeup/concentration, spacing of functional ligands, spacing between functional ligands and a substrate, and/or any other appropriate variation in binding conditions.

In some embodiments, the functional ligands included in a collection may be randomized or unknown. In other embodiments, at least one of the functional ligands may be selected previously for a known or suspected trait or characteristic, such as known binding to a particular target, predicted or observed structural changes during binding events, and/or any other known or suspected trait or characteristic. This may be desirable, for example, to efficiently utilize prior data or experimental results to speed up or narrow selection.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

The invention claimed is:

1. A method for selecting functional ligands comprising:
providing a library of biomolecules;
contacting said library with a target, said target comprising a target ionic species comprising arsenic (III) ion complexed with a coordination compound, said coordination compound selected from the group consisting of 4-(mercaptomethyl)benzoic acid, 1,4-benzenedimethanethiol, meso-2,3-dimercaptosuccinic acid, 2,3-dimercapto-1-propanesulfonic acid, and 2,3-dimercapto-1-propanol;
sequestering members of said library which bind to said target, wherein said members bind via non-Watson-Crick and non-covalent binding;
determining the composition or sequence of said members which bind to said target.

2. The method of claim 1, further comprising an enrichment step of contacting said members which bind to said target with said target and sequestering members of said library which bind again to said target prior to determining the composition or sequence for a number of times.

3. The method of claim 1, wherein said biomolecules are selected from the group consisting of single-stranded nucleic acids, peptide molecules and artificially modified versions thereof.

4. The method of claim 1, wherein said members which bind to said target comprise non-naturally occurring nucleic acid sequences.

5. The method of claim 1, wherein said target ionic species is protected from oxidation by addition of an antioxidant.

6. The method of claim 1, wherein said target ionic species is protected from oxidation by addition of ascorbic acid.

7. The method of claim 1, wherein said target is a molecular complex with the form selected from the group consisting of $As_2L_2$ or $As_2L_3$.

8. The method of claim 1, wherein said coordination compound adopts a conformation when complexed with said target ionic species via reversible arsenic (III) to sulphur bond(s).

9. The method of claim 1, wherein said coordination compound adopts a conformation when complexed with said target ionic species comprising a trigonal-pyramidal geometry.

10. The method of claim 4, enrichment step enriches for members which bind at a higher affinity than said members prior to said enrichment step.

* * * * *